United States Patent [19]
Imran

[11] Patent Number: 5,680,860
[45] Date of Patent: Oct. 28, 1997

[54] MAPPING AND/OR ABLATION CATHETER WITH COILABLE DISTAL EXTREMITY AND METHOD FOR USING SAME

[75] Inventor: Mir A. Imran, Palo Alto, Calif.

[73] Assignee: Cardiac Pathways Corporation, Sunnyvale, Calif.

[21] Appl. No.: 550,778

[22] Filed: Oct. 31, 1995

Related U.S. Application Data

[63] Continuation of Ser. No. 277,960, Jul. 20, 1994, abandoned, which is a continuation-in-part of Ser. No. 271,867, Jul. 1, 1994.

[51] Int. Cl.$^6$ .............................. A61B 5/04; A61N 1/36
[52] U.S. Cl. .................. 128/642; 607/122; 606/41
[58] Field of Search .......................... 128/642; 607/98, 607/99, 101, 102, 104, 105, 115, 116, 119, 122, 123, 125–128; 606/41, 47

[56] References Cited

U.S. PATENT DOCUMENTS

| | | |
|---|---|---|
| 4,522,212 | 6/1985 | Gelinas et al. . |
| 4,860,769 | 8/1989 | Fogarty et al. ........................ 607/122 |
| 4,865,037 | 9/1989 | Chin et al. ............................ 607/122 |
| 4,940,064 | 7/1990 | Desai . |
| 5,010,894 | 4/1991 | Edhag . |
| 5,016,808 | 5/1991 | Heil, Jr. et al. ....................... 607/122 |
| 5,052,407 | 10/1991 | Hauser et al. ........................ 607/122 |
| 5,237,996 | 8/1993 | Waldman et al. . |
| 5,239,999 | 8/1993 | Imran .................................... 607/127 |
| 5,279,299 | 1/1994 | Imran .................................... 607/126 |
| 5,334,193 | 8/1994 | Nardella ................................ 606/41 |
| 5,462,545 | 10/1995 | Wang et al. ........................... 606/41 |
| 5,476,495 | 12/1995 | Kordis et al. ......................... 607/122 |
| 5,487,385 | 1/1996 | Avitall ................................... 128/642 |

FOREIGN PATENT DOCUMENTS

| | | | |
|---|---|---|---|
| 4025369 | 7/1991 | Germany ........................... 128/642 |
| 5049701 | 3/1993 | Japan ................................. 607/122 |

*Primary Examiner*—Jeffrey R. Jastrzab
*Attorney, Agent, or Firm*—Flehr Hohbach Test Albritton & Herbert LLP

[57] ABSTRACT

A mapping and/or ablation catheter for introduction into a chamber having a wall accessible by a passage leading to the chamber. The catheter includes a flexible elongate member extending along a longitudinal axis and having a distal extremity. An elongate flexible element is provided and has one end secured to the distal extremity of the flexible elongate member and an opposite free end. The elongate flexible element is movable between a first position in which it is adaptable to conform generally to the contour of the passage and a second position in which it has a coil-like configuration. The elongate flexible element serves to form at least one electrode. The elongate flexible element is passed through the passage into the chamber when in the first position and the at least one electrode is moved into engagement with the wall for mapping and/or ablating of the wall when the elongate flexible element is in the second position.

27 Claims, 4 Drawing Sheets

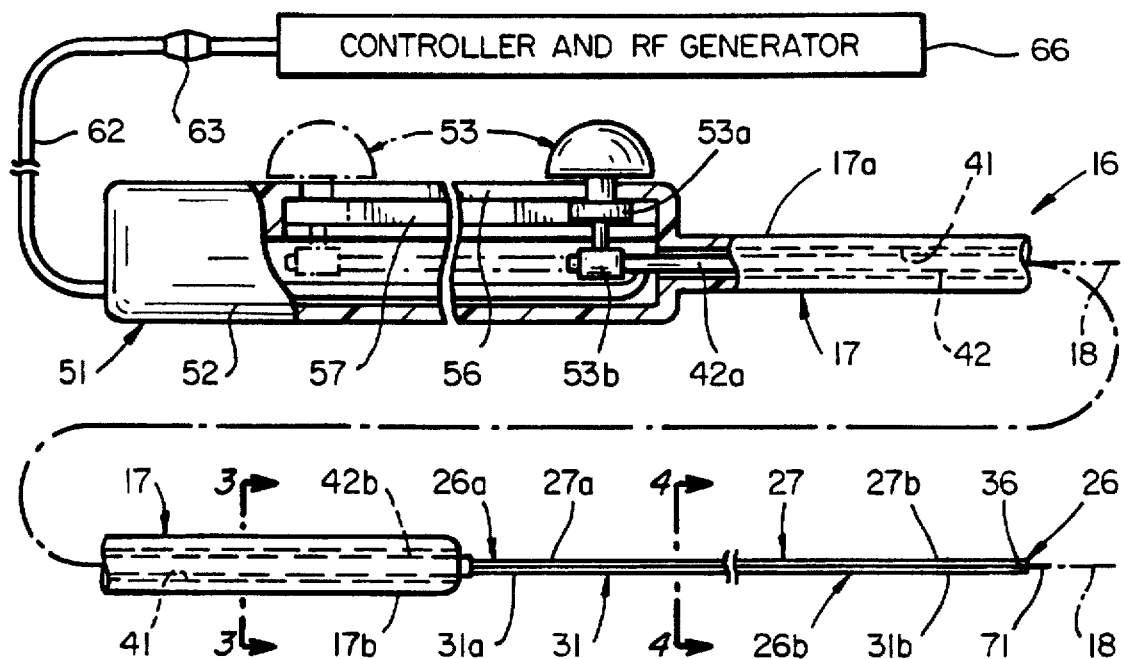
FIG_1
FIG_2
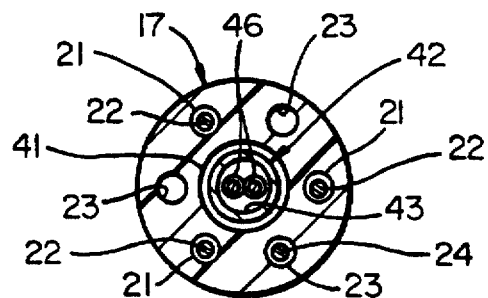
FIG_3

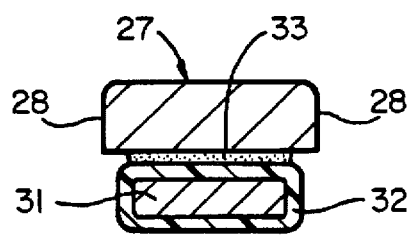
FIG_4
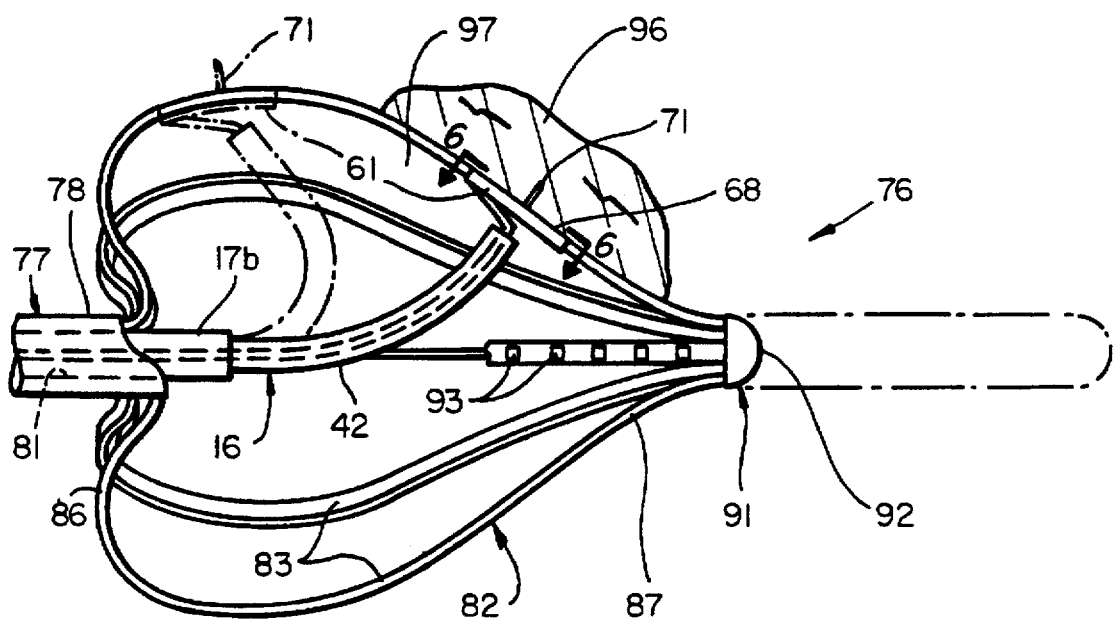
FIG_5
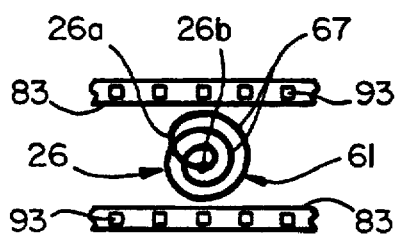
FIG_6
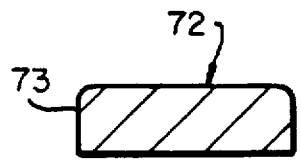
FIG_7

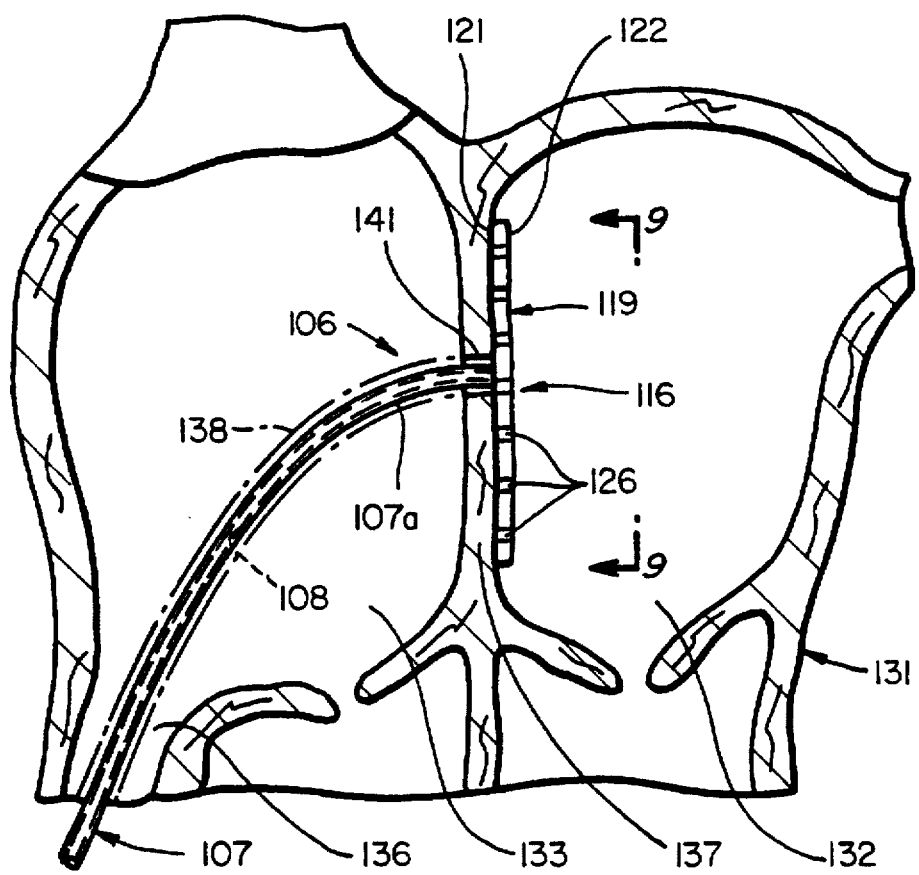
FIG_8
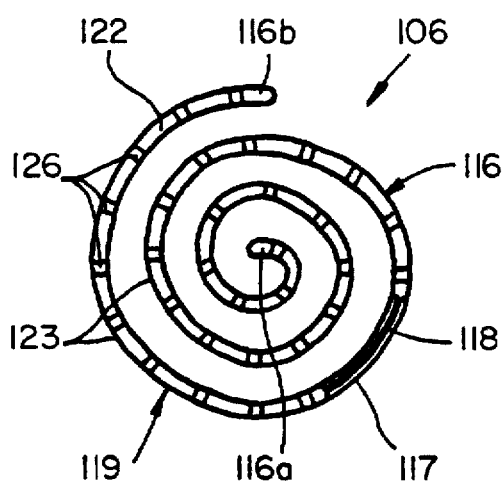
FIG_9
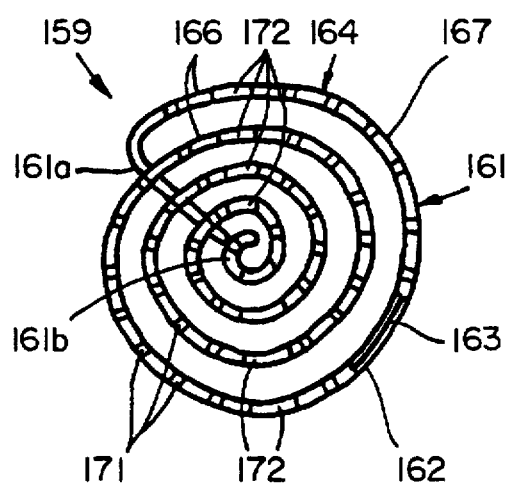
FIG_10

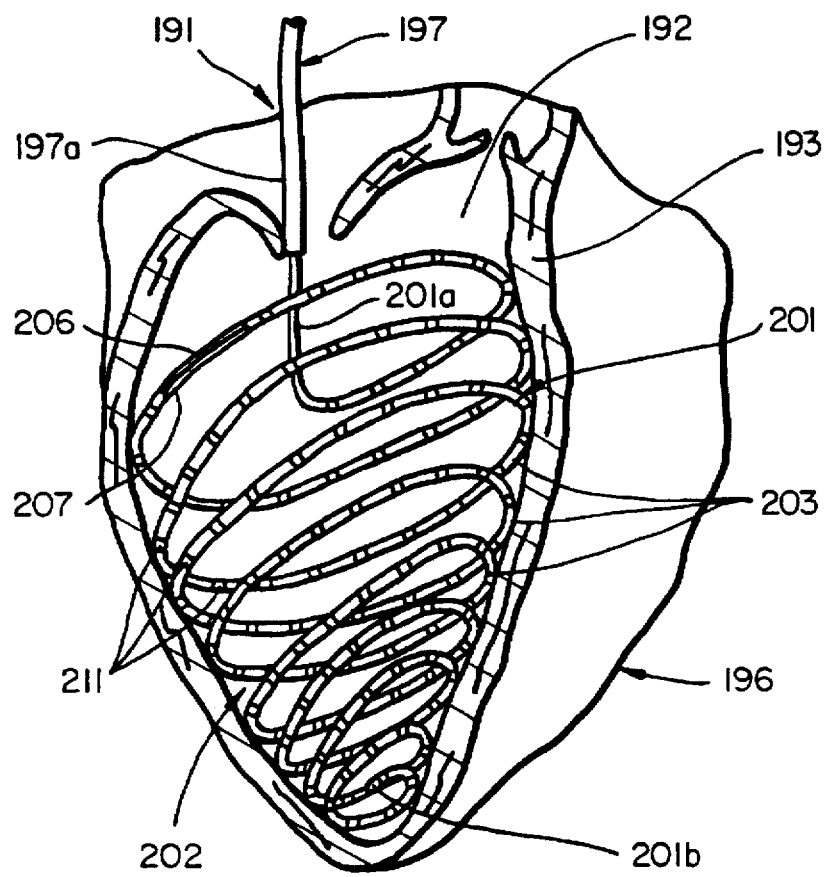
FIG_11
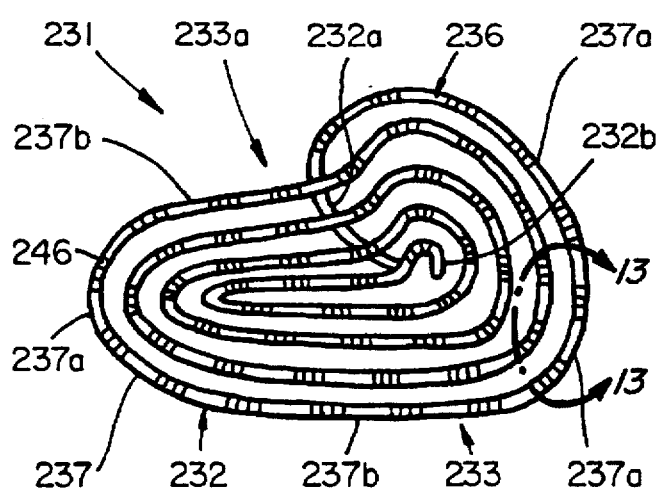
FIG_12
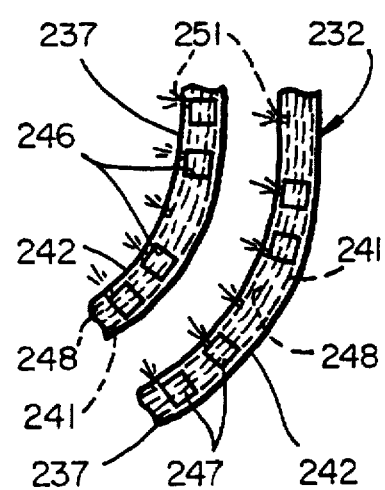
FIG_13

1

MAPPING AND/OR ABLATION CATHETER WITH COILABLE DISTAL EXTREMITY AND METHOD FOR USING SAME

CROSS-REFERENCES TO RELATED APPLICATIONS

This application is a continuation of U.S. patent application Ser. No. 08/277,960 filed Jul. 20, 1994, now abandoned which is a continuation-in-part of U.S. patent application Ser. No. 08/271,867 filed Jul. 1, 1994.

BACKGROUND OF THE INVENTION

1. Field of the Invention

This invention pertains generally to catheters for introduction into a human body and, more particularly, to a catheter for mapping and/or ablating a wall of a chamber in a human body.

2. Description of the Related Art

Catheters have been provided for introduction into a human body to map and/or ablate the walls of a chamber such as the heart. In general, however, these catheters neither permit high density mapping of the wall nor do they have relatively large ablation surfaces to form a continuous and large lesion across the wall of the chamber. Because of the foregoing, there is a need for a new and improved catheter which overcomes the above named disadvantages.

OBJECTS OF THE INVENTION

In general, it is an object of the present invention to provide a catheter with a distal extremity which when introduced into a chamber is coilable into a coil-like configuration for mapping and/or ablating of the wall of the chamber.

Another object of the invention is to provide a catheter of the above character in which the coil-like configuration lies substantially in a single plane.

Another object of the invention is -to provide a catheter of the above character in which the coil-like configuration serves as a large surface area ablation electrode.

Another object of the invention is to provide a catheter of the above character in which the coil-like configuration carries a plurality of electrodes to permit high density mapping of the wall of the chamber.

Another object of the invention is to provide a catheter of the above character in which the coil-like configuration carries a plurality of linearly aligned ablation electrodes so as to form a relatively continuous lesion across the wall of the chamber.

Another object of the invention is to provide a catheter of the above character in which the coil-like configuration is irregular shaped to accommodate the wall of the chamber.

Another object of the invention is to provide a catheter of the above character in which the coil-like configuration is helical in shape to permit circumferential mapping of the walls of the chamber.

Additional objects and features of the invention will appear from the following description from which the preferred embodiments are set forth in detail in conjunction with the accompanying drawings.

BRIEF DESCRIPTION OF THE DRAWINGS

FIG. 1 is a side elevational view, partially sectioned, of a catheter of the present invention with a coilable distal extremity for ablation.

FIG. 2 is a side elevational view showing a portion of the catheter of FIG. 1 in a second condition.

FIG. 3 is a cross-sectional view of the catheter of FIG. 1 taken along the line 3—3 of FIG. 1.

FIG. 4 is a cross-sectional view of the catheter of FIG. 1 taken along the line 4—4 of FIG. 1.

FIG. 5 is a side elevational view, partially cut away, of the catheter of FIG. 1 in use with a mapping catheter.

FIG. 6 is a plan view of the coilable distal extremity of the catheter of FIG. 1 taken along the line 6—6 of FIG. 5.

FIG. 7 is a cross-sectional view, similar to FIG. 4, of another embodiment of the catheter of the present invention with a coilable distal extremity for ablation.

FIG. 8 is a side elevational view of another embodiment of the catheter of the present invention with a coilable distal extremity mapping a chamber of the heart.

FIG. 9 is a plan view of the catheter of FIG. 8 taken along the line 9—9 of FIG. 8.

FIG. 10 is a plan view of another embodiment of the catheter of the present invention with a coilable distal extremity for mapping and ablation.

FIG. 11 is a side elevational view of another embodiment of the catheter of the present invention with a coilable distal extremity mapping a chamber of the heart.

FIG. 12 is a plan view of another embodiment of the catheter of the present invention with a coilable distal extremity for mapping.

FIG. 13 is an enlarged view of the catheter of FIG. 12 taken along the line 13—13 of FIG. 12.

SUMMARY OF THE INVENTION

In general, the mapping and/or ablation catheter of the present invention is for introduction into a chamber having a wall accessible by a passage leading to the chamber and includes a flexible elongate member extending along a longitudinal axis and having a distal extremity. An elongate flexible means is provided and has one end secured to the distal extremity of the flexible elongate member and an opposite free end. The elongate flexible means is movable between a first position in which it is adaptable to conform generally to the contour of the passage and a second position in which it has a coil-like configuration. The elongate flexible means is included within means forming at least one electrode. The elongate flexible means is passed through the passage into the chamber when in the first position and the at least one electrode is moved into engagement with the wall for mapping and/or ablating of the wall when the elongate flexible means is in the second position.

DETAILED DESCRIPTION

The catheter of the present invention can be a steerable catheter of the type described in co-pending application Ser. No. 08/134,487 filed Oct. 12, 1993, now U.S. Pat. No. 5,389,073. Steerable catheter 16 is approximately 2 French to 3 French in size and includes a flexible elongate tubular member or tube 17 made from plastic or any other suitable material. Tube 17 has proximal and distal extremities 17a and 17b and extends along a central longitudinal axis 18. The tube is generally circular in cross-section and is sized with an external diameter of approximately 0.09 centimeter.

Tube 17 is provided with a plurality of circumferentially disposed flexible elongate elements having a negative coefficient of expansion for bending distal extremity 17b in the manner described in co-pending application Ser. No. 08/134, 487 filed Oct. 12, 1993, now U.S. Pat. No. 5,389,073. In this regard, tube 17 is provided with at least three circumferentially disposed lumens and, as illustrated in FIG. 3, three peripheral lumens 21 disposed 120° apart about longitudinal axis 18 and extending the length of tube 17. Flexible elongate elements 22 having a negative coefficient of expansion are disposed in each peripheral lumen 21 at distal extremity 17b of tube 17 and are connected to conductors (not shown) which extend to proximal extremity 17a. At least one and as shown three additional circumferentially disposed lumens 23 extend the length of tube 17 and a common ground return element 24 extends through one of additional lumens 23 and is connected at its distal end to the distal ends of elements 22. Means (not shown) such as that disclosed in co-pending application Ser. No. 08/134,487 filed Oct. 12, 1993, now U.S. Pat. No. 5,389,073 is provided for adjusting the location of bend in distal extremity 17b of steerable catheter tube 17.

An elongate flexible means in the form of an ablation element 26 having proximal and distal extremities 26a and 26b is carried by distal extremity 17b of tube 17 and extends generally along longitudinal axis 18 (see FIGS. 1 and 4). Ablation element 26 includes a flexible element or ribbon 27 which is formed from a shape memory alloy, as for example a nickel-titanium alloy such as (Nitinol), and has proximal and distal ends 27a and 27b and first and second opposite side surfaces 28. By way of example, ribbon 27 is generally rectangular in cross-sectional shape, as illustrated in FIG. 4, and has a thickness of approximately 0.008 centimeter and a width of approximately 0.025 centimeter. A second flexible element or ribbon 31 underlies ribbon 27 and is made from any suitable material such as copper-silver and has proximal and distal ends 31a and 31b. Ribbon or strip 31 is encapsulated with an enamel coating 32 and, together with the enamel coating, has a thickness of approximately 0.008 centimeter. The enamel coated strip 31 is secured to ribbon 27 by any suitable means such as adhesive 33 which extends between ribbon 27 and strip 31 along the length thereof at a thickness of approximately 0.001 centimeter. Distal end 27b of conductive ribbon 27 and distal end 31b of conductive strip 31 are connected by any suitable conductive means such as spot weld 36.

Tube 17 is provided with a central lumen 41 for receiving and housing ablation element 26 during introduction of steerable catheter 16 into the chamber of an organ such as the heart. Central lumen 41 extends the length of tube 17 and is generally centered on longitudinal axis 18. A flexible elongate or tubular member 42 having proximal and distal end portions 42a and 42b and made from a suitable material such as stainless steel or (Nitinol) is slidably carried within central lumen 41. Proximal extremity 26a of ablation element 26 is mounted to distal end portion 42b in any suitable manner such as that described in co-pending application Ser. No. 07/983,968 filed Dec. 1, 1992, now U.S. Pat. No. 5,327,889 and in this manner is secured to distal extremity 17b of tube 17. Distal extremity 26b of ablation element 26 is not connected or otherwise secured to tube 17 and as such is characterized as a free end. Tubular member 42 is provided with a central passage or bore 43 and two insulated conductors 46 extend through the bore. One of insulated conductors 46 is electrically connected to proximal end 27a of ribbon 27 and the second insulated conductor is electrically connected to proximal end 31a of strip 31.

A hand-held control mechanism or handle 51 which can be of various types is mounted on proximal extremity 17a and forms a part of steerable catheter 16. Handle 51 consists of a two-part housing 52 which is formed of a suitable material such as plastic and is sized so that it can readily fit in the human hand. Control means (not shown) electrically connected to elements 22 and 24 can be included in handle 51 for controlling the amount and angle of bend in distal extremity 17b of tube 17 and for controlling the location of bend in distal extremity 17b. It should also be appreciated that this control means can include a separate joy stick and/or a separate variable current supply as described in co-pending application Ser. No. 07/983,962 filed Dec. 1, 1992, now abandoned and be within the scope of the present invention. Alternately, steerable catheter 16 can be of the type having actuatable pull wires and be within the scope of the present invention.

An activation means or mechanism is carried by a housing 52 for causing slidable movement of tubular member 42 and ablation element 26 secured thereto relative to tube 17 and includes a control member or thumb slide 53 which extends outwardly from the housing. Thumb slide 53 travels in a slot 56 which extends longitudinally of the housing and has a length which generally corresponds to the length of ablation element 26. The thumb slide has a guide portion 53a which rides in guide channel 57 of housing 52 and a sleeve portion 53b mounted about proximal end portion 42a of tubular member 42. As can be appreciated by those skilled in the art, movement of thumb slide 53 to a distal position, as shown in solid lines in FIG. 1, causes ablation element 26 to extend from distal extremity 17b of tube 17. Movement of the thumb slide to a proximal position, shown in dotted lines in FIG. 1, causes the ablation element to retract within central lumen 41 as shown in the fragmentary view of tube distal extremity 17b in FIG. 2.

Ablation element 26 is moveable between a first position in which the ablation element is adaptable to conform generally to the contour of the passage leading to the heart and a second position in which the ablation element has a coil-like configuration so as to a form a coil or plaque 61 lying substantially in a single plane. In this regard, ribbon 27 has been programmed with a memory which, when an electrical current is supplied to the same to increase its temperature, ribbon 27 stiffens to assume the programmed coil-like configuration. For so electrically activating ribbon 27, the two insulated conductors 46 extend through handle 51 to a cable 62 extending from the handle. Cable 62 has a connector 63 to permit electrical connection of steerable catheter 16 to a control unit or console 66. As so electrically coupled to ablation element 26, control console 66 is included within the means of the apparatus or system of the present invention for applying electrical energy to the ablation element so as to move the ablation element from its first position to its second position. It should be appreciated that other means of heating ribbon 27 can be provided and be within the scope of the present invention. For example, adjacent heating means such as that disclosed in co-pending application Ser. No. 08/044,255 filed Apr. 7, 1993, now abandoned can be provided.

When ablation element 26 is in its second position, shown generally in FIGS. 5 and 6, proximal end portion 26a extends outwardly from tubular member 42 to the radial extremity of coil 61. The portion of ablation element 26 forming coil 61 curves radially inwardly so as to form a plurality of turns 67 in the coil. Each of turns is generally circular in shape. Coil 61 has a diameter ranging from 0.5 to 2.0 centimeters, and preferably approximately one centimeter. Turns 67 of coil are spaced apart from each other a generally equal distance ranging from approximately 0.5 to 5.0 millimeters.

Steerable catheter 16 is provided with fixation means for engaging the wall of the heart and for retaining coil 61 in a predetermined position on the wall of the heart during beating of the heart. The fixation means includes fiber or needle 71 made from any suitable material such as plastic and mounted to free end 26b of ablation element 26 so as to extend therefrom generally along longitudinal axis 18. Fixation fiber 71 has a transverse dimension or diameter of approximately 0.01 centimeter ribbon 27 is programmed with a memory such that free end 26b and fixation fiber 71 mounted thereon curve outwardly at an approximate right angle from the plane of coil 61 when the ablation element is in its second or coil-like configuration. When fixation fiber 71 is so aligned relative to coil 61, the tip or end of the fixation fiber is spaced from the plane of coil 61 a distance ranging from approximately 0.025 to 0.254 centimeter.

Ablation element 26 is included within the means of steerable catheter 16 for forming at least one electrode for ablating the wall of the heart. When the ablation element has been reconfigured to its second position to form coil 61, the side surface 28 of the ablation element facing away from distal extremity 17b of tube 17 lies substantially in a single plane and forms a single electrode having a relatively large ablation surface 68. Control console 66 includes means for supplying radio frequency energy to ablation element 26. More specifically, once the ablation element has been reconfigured to form coil 61, the transmission through cable 62 and insulated conductors 46 of the electrical energy utilized for transforming the ablation element to its second position is ceased and radio frequency energy is then transmitted from the control console through the cable and insulated conductors to ribbon 27 for performing ablations therewith. Alternatively, the radio frequency energy can be transmitted over the electrical energy provided to ablation element 26 so as to activate ribbon 27.

In operation and use, steerable catheter 16 can be used in conjunction with a mapping catheter 76 such as that disclosed in co-pending application Ser. No. 08/044,255 filed Apr. 7, 1993, now abandoned. As disclosed therein and as illustrated in FIG. 5, mapping catheter 76 includes a flexible elongate tubular member or shaft 77 which is formed of a suitable material such as plastic and is circular in cross-section. Shaft 77 has a distal end portion 78 and is provided with at least one lumen 81 which extends along the length thereof. An electrode assembly 82 in the form of a basket is mounted on distal end portion 78 and is provided with a plurality, as for example eight, circumferentially spaced-apart longitudinally extending arms 83 having proximal and distal extremities 86 and 87. Arms 83 have an outwardly bowed shape memory and have their proximal extremities secured to distal end portion 78 of shaft 77. Distal extremities 87 of arms 83 are interconnected and mounted in a hub 91 having a rounded forward extremity 92. A plurality of electrodes 93 are mounted on each arm 83 in longitudinally spaced positions for mapping the wall of the heart. Arms 83 are moveable between a first or retracted position for insertion into the heart and a second or outwardly bowed position for mapping wall 96 of the heart. When in their outwardly bowed position, arms 83 generally define an interior region 97.

Once mapping catheter 76 has been introduced into the heart in the manner described in co-pending application Ser. No. 08/044,255 filed Apr. 7, 1993, now abandoned and heart wall 96 has been mapped, steerable catheter 16 can be utilized for ablating regions of heart wall 96. Steerable catheter 16 is introduced into the heart via mapping catheter. Preparatory to entry into the human body, ablation element 26 is disposed within central lumen 41 of tube 17 of steerable catheter 16. When ablation element 26 is in its first position, as shown generally in FIGS. 1 and 2, the ablation element is generally flaccid and flexible so as to permit its disposition in central lumen 41 and its travel through the tortuosities of the vascular system leading into the heart. Distal extremity 17b of tube 17 of the steerable catheter is inserted into lumen 81 of the mapping catheter and slid therethrough until distal extremity 17b extends through distal end portion 78 of the mapping catheter into interior region 97.

Once the distal end of steerable catheter 16 is within the heart, ablation element 26 is extended distally from passage 43 of tubular member 42 to its deployed position and electrical energy from control console 66 is applied to ribbon 27 so as to form the ablation element into coil 61 located distal of catheter tube 17. The transition temperature of ablation element 26 is set slightly higher than the body temperature of 37° C., as for example 42 to 45° C., so that the ablation element does not undesirably reconfigure prior to proper placement within the body. The current supplied by control console 66 is carried by one of insulated conductors 46 to ribbon 27 and then spot weld 36, which permits the current to travel back through conductive strip 31 and the other insulated conductor 46.

Coil 61 engages a predetermined portion of heart wall 96 exposed between two adjacent arms 83 of mapping catheter 76 through a combination of bending distal extremity 17b of tube 17 of steerable catheter 16, rotation of the steerable catheter within lumen 81 of mapping catheter 76 and further extension of distal extremity 17b into interior region 97 of the mapping catheter. The engagement of fixation needle 71 with the heart wall assists in guiding coil 61 to and retaining the coil at its desired location on heart wall 96. When so engaged with the heart wall, the plane of coil 61 can be aligned at various angles relative to longitudinal axis 18 of tube 17. For example, coil 61 can be aligned at an approximate right angle to tube 17, as shown in solid lines in FIG. 5, or at an oblique angle to tube 17, as shown in phantom lines in FIG. 5.

When coil 61 is so placed against heart wall 96, ablation surface 68 is in general engagement with the heart wall. Radio frequency energy ranging from 300 KHz to 1 MHz can thereafter be supplied by control console 66 through cable 62 and insulated conductors 46 to ribbon 27 for ablating the heart wall and creating lesions thereon. A suitable power level ranges from 5 to 70 watts and a suitable duration ranges from 30 to 240 seconds. The spacing between turns 67 of coil 61 is sufficiently small so that the lesion created by each turn 67 overlaps the lesion created by the adjacent turn 67 and a generally continuous lesion is formed by ablation surface 68.

The cross-sectional area of ablation surface 68 is sufficient to create a lesion on heart wall 96 of a relatively large size. Thus, the method and apparatus of the present invention creates a relatively large lesion without the need of a relatively large two-dimensionally continuous plate-like electrode having a surface area approximating the size of the lesion to be created. Instead, catheter 16 having a relatively small diameter which can be easily passed through the vascular system is utilized. The spacing between coil turns 67 is sufficient to permit blood to pass through coil 61 while in the heart.

The inward curvature of turns 67 of coil 61 facilitates movement of ablation element 26 within the interior region 97 of electrode assembly 82 and the chamber of the heart. More in particular, coil 61 does not have a free end located at the outer periphery thereof for catching on valves or other protrusions in or near the chamber of the heart being ablated or for catching on arms 83 or other portions of mapping catheter 76.

After completion of the ablation procedure, thumb slide 53 is moved proximally by the thumb of the operating physician so that ablation element 26 retracts into tube 17. Steerable catheter 16 is then removed from lumen 81 of mapping catheter 76 and the mapping catheter removed from the interior of the body in which the procedure was performed.

Steerable catheter 16 can be used other than in connection with a catheter such as mapping catheter 76. For example, steerable catheter 16 can be introduced into a heart or into another chamber in a body with the aid of a guide catheter or otherwise for performing ablations therein.

It should be appreciated that the ablation coil of the steerable ablation catheter of the present invention can have other configurations and constructions and be within the scope of the present invention. For example, the ablation element could be programmed with a memory which forms a coil which is other than circular when required to ablate portion of the heart wall. The generally planar coil could be rectangular or square-shaped or be formed of generally arcuate turns which form a non-circular or irregular coil. In addition, an ablation element having a free end and formable into a coil having only a single turn or even less than a single turn would be within the scope of the present invention. In addition, the ablation element of the present invention could be provided with a plurality of ablation electrodes formed along the length thereof which are of sufficient size and spaced sufficiently close to each other so that when the ablation element is reconfigured to a coil-like configuration the individual lesions created by these spaced electrodes overlap to generally form a single large lesion.

Furthermore, the ablation element of the steerable catheter of the present invention can be formed with a shape memory element which does not require heating to achieve the desired shape or characteristic. For example, as illustrated in FIG. 7, an ablation element 72 could be provided having a ribbon 73 which is formed from a suitable material such as (Nitinol) and is programmed with a shape and exhibits superelasticity when in its programmed shape. As discussed more fully in co-pending application Serial No. 08/044,255 filed Apr. 7, 1995, now abandoned, ribbon 72 has a recoverable strain in excess of 1.0%. The superelastic ribbon 72 has a transition temperature of approximately 0° C., significantly below body temperature, so that when at room or body temperature it always takes on the shape given to it during annealing. Once within the body, change in the shape of the superelastic ribbon 72 is induced not by a temperature change, but instead by the application of external stress.

Ablation element 72 does not require an electrical energy source for thermally activating its reconfiguration. Accordingly, strip 31 which served as a return for the electrical activation energy is not required. Instead, the tubular shaft of the catheter serves to apply the necessary external stresses for reconfiguring ablation element 72 and, as such, is included within the means of the catheter for moving ablation element 72 between its first and second positions. An activation mechanism such as thumb slide is included within the means for moving the ablation element between a first position in which the ablation element is substantially within a lumen, such as central lumen 41, of the tubular shaft and a second position in which the ablation element extends from the distal extremity of the catheter shaft.

In the operation of a steerable catheter having an ablation element formed with a shape memory alloy exhibiting superelasticity, the ablation element has a coil-like configuration when free from external stress. Prior to use, the ablation element is retracted into the central lumen, such as central lumen 41, of the catheter shaft. The stress applied upon the ablation element during its entry into the central lumen causes the ablation element to reconfigure to a shape generally corresponding to that of the central lumen. Once the distal extremity of the steerable catheter has been introduced into interior region 97 in the manner discussed above, the ablation element is deployed from the catheter shaft with the aid of a thumb slide similar to slide 53. As the ablation element extends from the catheter shaft, it recovers to its predetermined shape. Once the ablation element has been so reconfigured into an ablation coil, the steerable catheter places the coil at the desired location on the heart wall in the manner discussed above for ablating the tissue of the heart wall.

It should be further appreciated that the shape memory element of ablation element 26 can be made from a suitable plastic or metal such as stainless steel which is deformable upon the application of external stresses. A steerable catheter provided with such an ablation element would also be within the scope of the present invention.

In addition, a steerable catheter 16 having a nonretractable thermally or electrically activated ablation element, such as ablation elements 26 or 72, mounted to distal extremity 17b so as to permanently extend distally therefrom would also be within the scope of the present invention. The relative flexibility of such an ablation element when it is in its first or non-activated condition facilitates its passage through the vascular system of the body without the need of the ablation element being retracted within a shielding tube such as tube 17. A steerable catheter of this type is introduced into the desired chamber of a body through the aid of a guiding catheter, possibly in conjunction with a catheter such as mapping catheter 76. Once the distal end of the guiding catheter has been introduced into the desired chamber, the ablation element is pushed from the guiding catheter into the chamber and thereafter electrically activated and steered by the radio frequency generator of the steerable catheter.

The mapping and/or ablation catheter with coilable distal extremity of the present invention can have other embodiments. For example, a steerable mapping catheter 106 substantially similar to steerable catheter 16 is illustrated in FIGS. 8 and 9. Catheter 106 can range from 2 French to 10 French and includes a flexible elongate tubular member or shaft 107 having a distal extremity 107a and at least one lumen 108 extending along the length thereof. A flexible elongate means or element 116 is provided and has a proximal end portion 116a carried by shaft distal extremity 107a and an opposite distal or free end portion 116b. The flexible element is generally circular in cross-section and has a transverse dimension or diameter ranging from approximately 0.066 to 0.330 centimeter. An outer tubular member or sheath 117 made from any suitable non-conductive material such as plastic extends around the outside of flexible element 116 along the length thereof.

Flexible element 116 is moveable between a first position in which the flexible element conforms generally to the contours of lumen 108 of the catheter shaft and a second position in which the flexible element has a generally coil-like configuration as shown in FIGS. 8 and 9. The flexible element includes an internal wire or filament 118 carried within sheath 117 made from a suitable shape memory alloy material such as (Nitinol) which is either thermally activated or exhibits superelasticity. As more fully discussed above, the programmed shape of thermally activated (Nitinol) is temperature induced while the programmed shape of superelastic (Nitinol) can be changed by the application of external stresses. It should also be appreciated that filament 118 could be made from a shape memory plastic and be within the scope of the present invention.

When flexible element 116 is in its second position, it assumes a coil-like configuration in the form of a generally planar coil 119 having a proximal surface 121 and a distal surface 122. Coil 119 is generally circular in shape and is formed from a plurality of generally circular loops or turns 123 which curve radially outwardly from proximal end portion 116a. As shown, flexible element 116 is formed with approximately three turns 123. Adjacent turns 123 are equally spaced from each other a distance ranging from approximately one to five millimeters and coil 119 has a transverse dimension or diameter ranging from approximately 0.5 to 3.0 centimeters.

An electrode assembly comprised of a plurality of ring electrodes 126 is carried by flexible element 116 for mapping the wall of a chamber within the body. As such, flexible element 116 serves as the distal extremity of mapping catheter 106 for carrying a plurality of electrodes and is included within the means of mapping catheter 106 for forming at least one electrode. Ring electrodes 126 are made from any suitable material such as gold-plated copper or platinum iridium and are mounted about flexible element 116 by any suitable means such as that disclosed in co-pending application Ser. No. 08/071,659 filed Jun. 2, 1993, now abandoned. Sheath 117 is included within the means for mounting electrodes 126 to flexible element 116. Adjacent electrodes 126 are spaced apart from each other along the length of flexible element 116 a generally equal distance ranging from approximately one to ten millimeters. The electrodes are electrically connected to a plurality of leads or traces (not shown) which extend through flexible element 116 and through catheter shaft 107 to the handle of the catheter.

In operation and use, mapping catheter 106 can be used for mapping within an organ such as a heart 131 having chambers in the form of left and right atriums 132 and 133 or left and right ventricles. Left atrium 132 is accessible by a passage such as femoral vein 136. The left and right atriums are separated by septal wall 137.

In the method of use of mapping catheter 106, left atrium 132 is accessed from right atrium 133 in a conventional manner such as, for example, by penetrating septal wall 137 with a steerable guide catheter 138 of a conventional type having a trocar (not shown) therein to create a passageway or opening 141 through the septal wall. After guide catheter 138 has been pushed through opening 141 and the trocar removed from the guide catheter, flexible element 116 of the mapping catheter is slid through guide catheter 138 so as to be introduced through opening 141 into left atrium 132. In a manner similar to that discussed above with respect to steerable catheter 16, flexible element 116 is reconfigured to form coil 119 either through thermal activation of the flexible element or retraction of a restraining sheath from around the flexible element. Coil 119, which is aligned relative to distal extremity 107a at a generally right angle, is pulled proximally until ring electrodes 126 on proximal surface 121 of the coil engage septal wall 137. The relatively closely spaced electrodes 126 are then utilized for performing high density mapping of the septal wall.

Although flexible element 116 has been shown with a plurality of 34 unipolar electrodes, a coil having a plurality of bipolar electrodes greater than four in number would be within the scope of the present invention. It should also be appreciated that the coil of mapping catheter 106 could be oval shaped or have other configurations dependent upon the size and shape of the area targeted for mapping.

A portion of another embodiment of a steerable mapping and ablation catheter with a coilable distal extremity is illustrated in FIG. 10. Catheter 159 can range from 2 French to 10 French in size and includes a flexible elongate tubular member or shaft (not shown) formed with a braided torquable shaft such as that disclosed in co-pending application Ser. No. 08/212,001 filed Mar. 24, 1994, now U.S. Pat. No. 5,478,330. An elongate flexible means or element 161 is included with a proximal end portion 161a secured to the distal extremity of the catheter shaft and a distal or free end portion 161b. Flexible element 161 is formed from an outer flexible tubular member or sheath 162 which is made from any suitable non-conductive material such as plastic and has a transverse dimension or diameter ranging from 2 to 10 French. A fiber or filament 163 extends inside sheath 162 over the length of the flexible element.

Fiber 163 is a shape memory alloy which is made from any suitable material such as (Nitinol) and has been programmed to assume a coil-like configuration in the form of generally planar coil 164. As more fully discussed above with respect to catheters 16 and 106, (Nitinol) fiber 163 can either be thermally or electrically activated to recover its shape or be of a superelastic type which can be deformed from its original shape by external stresses and reconfigurable to that shape upon release of the external stresses. When the fiber 163 is in its non-activated or stress-induced condition, as the case may be, flexible element 161 is adaptable to contour to the shape of the passage leading to the targeted chamber within the body. In the case of a thermally or electrically activated (Nitinol) fiber 163, the flexible element is generally flaccid in this first condition. In the case of a fiber 163 exhibiting superelasticity, the flexible element can be reversibly deformed so as to fit within the confines of a lumen in a catheter shaft.

Coil 164 is generally circular in shape and is formed from a plurality of turns 166 which each curve radially inwardly toward free end portion 161 located generally at the center of coil 164. The distance between adjacent turns 166 ranges from approximately one to five millimeters. Coil 164 has a non-continuous distal surface 167 and a transverse dimension or diameter ranging from approximately 0.5 to 3.0 centimeters so as to have a surface area ranging from 0.2 to 7.1 $cm^2$.

An electrode assembly having a plurality of electrodes is carried by flexible element 161 for mapping and ablating within a chamber in a body such as an atrium of the heart. More particularly, generally rectangular-shaped sensing or mapping electrodes 171 are formed on distal surface 167 of flexible element 161. It should be appreciated, however, that mapping electrodes 171 could be in the form of ring electrodes similar to ring electrodes 126 of mapping catheter 106 and be within the scope of the present invention.

An additional set of electrodes in the form of ablation electrodes 172 are also carried by flexible element 161 and are formed thereon so as to be generally linearly disposed across distal surface 167. In general, two diametrically opposed ablation electrodes 172 are provided on each complete turn 166 of coil 164 and the imaginary line created by the linearly disposed ablation electrodes generally intersects the center of coil 164. Ablation electrodes 172 are generally rectangular in shape and have a longitudinal dimension ranging from two to four millimeters and a transverse dimension ranging from 0.066 to 0.250 centimeter. Ablation electrodes 172 can also serve as mapping or sensing electrodes and be within the scope of the present invention.

Mapping and ablation electrodes 171 and 172 are generally equally spaced apart along the length of flexible element 161, with a distance between adjacent electrodes ranging from approximately two to five millimeters. As can be seen, flexible element 161 is included within the means of catheter 159 for forming at least one electrode and can be provided with up to several hundred electrodes. Flexible element 161 can include cooling means such as that disclosed in co-pending application Ser. No. 07/983,732 filed Dec. 1, 1992, now U.S. Pat. No. 5,348,554 for creating deep lesions in the tissue of the heart wall with ablation electrodes 172.

In operation and use, steerable catheter 159 is particularly advantageous for treating atrial fibrillation or arrhythmia as well as ventricular tachycardia. When used for treating atrial fibrillation or arrhythmia, flexible element 161 is introduced into the atrium of the heart in the manner discussed above while in its first position. Once inside the atrium, flexible element 161 is reconfigured to form coil 164. Distal surface 167 is brought into engagement with the desired portion of the wall of the chamber and mapping electrodes 171 permit high density mapping of the wall portion so engaged.

The linear array of ablation electrodes 172 can be aligned initially or through subsequent rotation of the steerable catheter 159 so as to be transverse to the direction of travel of the re-entry circuit or impulse being transmitted through the heart wall and causing the arrhythmia. Radio frequency energy is applied to ablation electrodes 172, either sequentially or simultaneously, so as to create a general linear lesion across the portion of the heart wall engaged by distal surface 167. The spacing between adjacent ablation electrodes 172 is sufficiently small so that the respective lesions created by the adjacent ablation electrodes overlap. In addition, the ablation electrodes have a sufficient longitudinal length so that such overlapping occurs even if the ablation electrodes are not in exact linear alignment due to relative misalignment between the respective turns 166 of coil 164 while in engagement with the heart wall.

In an alternate embodiment of catheter 159 not illustrated in the drawings, flexible element 161 can be internally provided with single or counterwound (Nitinol) coils for providing the desired shape of the flexible element. (Nitinol) coils of this type permit a relatively tight coil-like configuration for enhancing the density of the mapping and ablation electrodes and thus improving the performance of the catheter. Counterwound coils also inhibit undesirable bending of the flexible element during pushing and, as such, are desirable for use with flexible elements formed from superelastic (Nitinol) where the flexible element is pushed from the lumen of a catheter for reconfiguring to an ablation and/or mapping coil.

Mapping and/or ablation catheters of the present invention can be provided with flexible elements at the distal extremity which assume a coil-like configuration not lying substantially in a single plane. An embodiment of such a catheter is illustrated in FIG. 11 where a portion of mapping catheter 191 is illustrated within a chamber of an organ in a body such as right ventricle 192 formed by a wall 193 of heart 196. Mapping catheter 191 includes a flexible elongate tubular member or shaft 197 made from any suitable material such as plastic and having a distal extremity 197a. An elongate flexible means in the form of flexible element 201 is provided and has a proximal end portion 201a secured to shaft distal extremity 197a and an opposite distal end portion or free end portion 201b.

Flexible element 201 is moveable between a first position in which it conforms generally to the contour of the passage or vein through which the flexible element is introduced into heart 196 and a second position in which the flexible element has a generally coil-like configuration. More specifically, flexible element 201 is provided with a predetermined configuration to provide a predetermined conformation when in the second position so as to conform more closely to heart wall 193 of the ventricular and, when in its second position, is in the shape of a helical coil 202 formed with a plurality of turns 203. Proximal end portion 201a extends from shaft distal extremity 197a to the outer radial periphery of helical coil 202 so as to initiate the proximal-most turn 203 thereof. The arcuate turns 203 of helical coil 202 are generally circular in shape, although turns 203 could be half-moon or crescent in shape so as to better approximate the chamber being mapped and be within the scope of the invention. Turns 203 curve distally and radially inwardly so that helical coil 202 tapers inwardly as its extends from distal extremity 197a of shaft 197. Adjacent turns 203 are spaced apart a generally equal distance ranging from two to five millimeters, and helical coil 202 can be formed with turns 203 ranging from 1 to 20 in number. Distal-most turn 203 includes free end portion 201b of flexible element 201.

Flexible element 201 includes an internal tubular assembly 206 extending along the length of the flexible element so as to provide structural support to the flexible element when in its coil-like configuration. The tubular assembly consist of counterwound strips made from any suitable shape memory alloy such as (Nitinol) and programmed with a memory so as to recover to the shape of helical coil 202. The tubular assembly 206 can be either thermally or electrically activated or superelastic (Nitinol) as discussed above in more detail. Alternately, tubular assembly 206 can be made from composite tubing consisting of two or three thin-wall tubes having different durometers. The thin-wall tubes are fused together in a spiral mold having the shape of helical coil 202 so as to retain the shape of the helical coil over time. Flexible element 201 has a diameter ranging from 0.066 to 0.330 centimeter and is provided with an outer elongate tubular member or sheath 207 which extends around tubular assembly 206 over the length of the flexible element. Sheath 207 is made from any suitable materials such as nonconductive plastic.

A plurality of ring electrodes 211 ranging from approximately 10 to 200 in number and made from any suitable material such as gold-plated copper or platinum iridium comprise an electrode assembly carried by flexible element 201. In this manner, flexible element 201 is included within the means of catheter 191 for forming at least one electrode. Electrodes 211 are longitudinally spaced apart along the length of the flexible element a distance ranging from approximately two to four millimeters so as to form an array of high density mapping electrodes on helical coil 202. A plurality of leads (not shown) are carried within sheath 207 and are electrically connected at one end to respective mapping electrodes 211. These leads extend down flexible element 201 and shaft 197 so as to permit electrical signals detected by mapping electrodes 211 to be transmitted outside of the body. A microchip (not shown) with multiplexing capabilities can be included within flexible element 201 for facilitating transmission of the information detected by the electrodes to outside of the body.

In the operation of mapping catheter 191, flexible element 201 is introduced into right ventricle 192 through the tricuspid valve with the aid of a guide catheter in a manner similar to the deployment of the mapping apparatus disclosed in co-pending application Ser. No. 08/044,255 filed Apr. 7, 1993 now abandoned. When flexible element 201 is moved to its second position, the preprogrammed memory of flexible element 201 causes turns 203 to expand or bow outwardly so that mapping electrodes 211 mounted thereon engage wall 193 forming right ventricle 192 and sense the electrical signals thereon. Catheter 191 need not be of a steerable type because helical coil 202 generally engages the entire inner surface of the ventricle. The close relative spacing between adjacent mapping electrodes 211 and adjacent turns 203 permit high density mapping of heart wall 193. The radial inward curvature of turns 203 results in free end portion 201b being located at the apex of the right ventricle and inhibits snagging of free end portion 201b during movement of flexible element 201 within the ventricle. Mapping catheter 191 can be similarly operated in the left ventricle of the heart and be within the scope of the present invention.

A steerable ablation catheter such as that disclosed in co-pending application Ser. No. 07/983,962 filed Dec. 1, 1992, now abandoned can be used in conjunction with mapping catheter 191. The ablation catheter would be introduced interior mapping catheter 191 for performing ablations between turns 203 of helical coil 202.

In another embodiment, an irregular shaped mapping catheter is provided (see FIGS. 12 and 13). Mapping catheter 231 includes an elongate flexible means in the form of flexible element 232 having a proximal end portion 232a carried by the distal extremity of a catheter shaft (not shown) and an opposite distal end portion or free end portion 232b. Flexible element 232 is moveable between a first position for introduction into the chamber to be mapped and a second position in which the flexible element has a generally coil-like configuration which is irregular in shape as illustrated in FIG. 12. In its second position, the flexible element forms a coil 233 which is generally flat and has a generally planar mapping surface 236. Coil 233 is generally oblong in shape and is formed with an indented or recessed portion 233a. Proximal end portion 232a of flexible element 232 extends outwardly from the distal extremity of the catheter shaft to initiate the outermost turn 237 of coil 233. Each turn 237 is formed from arcuate portions 237a and generally straight portions 237b and curves radially inwardly so that free end portion 232b of the flexible element is generally at the center of coil 233. Adjacent turns 237 are spaced apart a generally equal distance ranging from one to five millimeters and coil 233 forms a mapping surface area ranging from three to ten square centimeters.

Flexible element 232 has an internal fiber or filament 241 made from any suitable shape memory alloy such as (Nitinol) which extends the length of the flexible element and has been programmed with the shape of coil 233. Filament 241, as discussed above, can be thermally or electrically activated to recover the shape of coil 233 or, as an alternative, can exhibit superelasticity so that coil 233 can be reconfigured by external stresses into a shape which permits its introduction via a catheter into the chamber to be mapped. A flexible elongate tubular member or sheath 242 made from any suitable material such as nonconductive plastic extends around the outside of flexible element 232. As so constructed, flexible element 232 has a transverse dimension or diameter ranging from 0.066 to 0.254 centimeter.

An array or assembly of mapping electrodes 246 is carried by mapping surface 236 of coil 233. Mapping electrodes 246 are arranged along the length of flexible element 232 in bipolar pairs 247. Adjacent mapping electrodes of a bipolar pair 247 are spaced apart a generally equal distance ranging from two to five millimeters, and adjacent bipolar pairs of mapping electrodes are spaced apart a generally equal distance ranging from two to ten millimeters. The mapping electrodes are made from any suitable conductive material such as gold-plated copper or platinum iridium and are generally rectangular in shape, although the mapping electrodes can have the shape of a ring which extends around the flexible element and be within the scope of the present invention. As can be seen, flexible element 232 is included within the means of catheter 231 for forming at least one electrode. The flexible element includes a plurality of traces or leads (not shown) which are electrically connected at one end to respective mapping electrodes 246 and extend down through the flexible element and the catheter shaft so as to permit electrical communication between mapping electrodes 246 and the outside of the body.

Means is included within flexible element 232 for inhibiting the coagulation of blood or other fluids within turns 237 of coil 233. This means includes at least one lumen 248 which extends the length of flexible element 232 along the inside thereof. A plurality of ports 251 are provided in flexible element 232 and are spaced apart along the length of the flexible element at generally equal distances ranging from approximately five to ten millimeters. Ports 251 are aligned about the flexible element so as to open radially inwardly of coil 233 toward an inner adjacent turn 247 and extend through outer sheath 242 for communication with lumen 248. Ports 251 are sized and configured so as to permit a pressurized fluid carried within lumen 248, such as a heparinized saline solution, to be dispensed from the flexible element in the form of a spray for washing the adjacent inner turn 247 and creating turbulence between turns 247.

In operation and use, mapping catheter 231 can be used to map a portion of a wall of a chamber such as an atrium or ventricle within the human heart. While in its first position, flexible element 232 is introduced into the chamber in a manner discussed above. Once within the chamber, the flexible element is reconfigured to form coil 233 for placement against the targeted portion of chamber wall. Recessed portion 233a permits the coil to navigate and engage the desired portion of the heart wall despite protuberances and other irregularities in the heart wall. Bipolar mapping electrodes 246 detect electrical signals in the heart wall for transmission outside of the body. The relative close spacing of mapping electrodes 246 permits high density mapping of the portion of the heart wall engaged by mapping surface 236. The plurality of sprays formed at ports 251 from the pressurized solution within lumen 248 serve to inhibit blood from coagulating on the relatively closely spaced turns 237 of coil 233. The coil can also be coated with an antithrombogenic material for inhibiting coagulation.

It should be appreciated that filament 241 of flexible element 232 can be programmed to form other irregular shapes required to permit mapping of other portions of the heart wall and be within the scope of the present invention.

From the foregoing, it can be seen that a new and improved catheter has been provided. The catheter includes a distal extremity which when introduced into a chamber is coilable into a coil-like configuration for mapping and/or ablating of the wall of the chamber. Catheters can be provided in which the coil-like configuration lies substantially in a single plane and in which the coil-like configuration serves as a large surface area ablation electrode. The coil-like configuration can carry a plurality of electrodes to permit high density mapping of the wall of the chamber and can carry a plurality of linearly aligned ablation electrodes so as to form a relatively continuous lesion across the wall of the chamber. The coil-like configuration can be irregular-shaped to accommodate the wall of the chamber and can be helical in shape to permit mapping of the periphery of the chamber.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, and to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A mapping and/or ablation catheter for introduction into a chamber formed by a wall of a heart of a human body comprising a flexible elongate tubular member having proximal and distal extremities and extending along a longitudinal axis, the flexible elongate tubular member provided with a lumen extending between the proximal and distal extremities and having a length so that when the distal extremity is disposed in the chamber of the heart the proximal extremity is outside of the body, a flexible elongate member slidably carried within the lumen and having a distal end portion with a free end, means carried by the proximal extremity of the flexible elongate tubular member for moving the distal end portion between a first position disposed in the lumen in the flexible elongate tubular member and a second position extending distally of the flexible elongate tubular member, the distal end portion including an element of a shape memory alloy having a predetermined coil-like configuration in which the distal end portion extends substantially in a plane at an angle to the longitudinal axis when in the second position, the distal extremity of the flexible elongate tubular member serving as means for moving the distal end portion to a substantially straightened configuration when the distal end portion is disposed in the lumen and a plurality of longitudinally spaced-apart electrodes carried by the distal end portion for permitting high density mapping and/or ablating of a portion of the wall inside the chamber of the heart.

2. A catheter as in claim 1 wherein the coil-like configuration extends at a substantially right angle to the longitudinal axis.

3. A catheter as in claim 1 wherein the coil-like configuration has a plurality of loops which are generally circular in shape.

4. A catheter as in claim 1 wherein the coil-like configuration has a plurality of loops which are asymmetrical in shape.

5. A catheter as in claim 1 wherein the coil-like configuration has an external diameter of at least 0.5 centimeter.

6. A catheter as in claim 1 wherein the coil-like configuration has a plurality of turns which curve radially inwardly.

7. A catheter as in claim 6 wherein the free end of the distal extremity extends generally at a right angle to the coil-like configuration for engaging the wall of the chamber and for retaining the coil-like configuration on the wall of the chamber.

8. A catheter as in claim 1 wherein the coil-like configuration has a plurality of turns which curve radially outwardly.

9. A catheter as in claim 1 wherein the plurality of electrodes includes a plurality of at least three ablation electrodes in substantial linear alignment across the coil-like configuration for forming a continuous lesion on the wall of the heart.

10. A catheter as in claim 1 wherein the coil-like configuration has a plurality of loops, the plurality of electrodes including at least one ablation electrode extending around at least one of the loops.

11. A catheter as in claim 1 wherein the element is made from a superelastic shape memory alloy.

12. A catheter as in claim 1 wherein the coil-like configuration extends in a plane at a substantially right angle to the longitudinal axis.

13. A mapping and/or ablation catheter for introduction into a chamber of a heart having a wall accessible by a passage leading to the chamber comprising a flexible elongate member extending along a longitudinal axis and having a distal extremity with a free end, the distal extremity having a first shape in which the distal extremity is substantially straight to permit the distal extremity to pass through the passage, means coupled to the flexible elongate member for applying electrical energy to the flexible elongate member to change the distal extremity to a second shape in which the distal extremity has a coil-like configuration extending in a plane at an angle to the longitudinal axis, at least one electrode carried by the distal extremity and being included within means for mapping and/or ablating the wall inside the chamber of the heart whereby the flexible elongate member is passed through the passage into the chamber when having the first shape and the at least one electrode is moved into engagement with the wall for mapping and/or ablating of the wall when the flexible elongate member has the second shape.

14. A mapping and/or ablation catheter for introduction into a chamber of a heart having a wall accessible by a passage leading to the chamber comprising a flexible elongate member extending along a longitudinal axis and having a distal extremity formed in a coil-like configuration with a plurality of turns, at least one electrode carried by the coil-like configuration and being included within means for mapping and/or ablating the wall of the chamber of the heart, the coil-like configuration being provided with a plurality of longitudinally spaced-apart ports and at least one lumen in communication with the ports for supplying a liquid to the ports for delivery between the turns of the coil-like configuration the at least one lumen and ports serving as means for inhibiting the formation of thrombus on the coil-like configuration.

15. A method of mapping a wall of a chamber of a heart having a surface utilizing a flexible elongate tubular member having proximal and distal extremities and a lumen extending between the proximal and distal extremities and a flexible elongate member having a distal end portion with a free end, the distal end portion including an element of a shape memory alloy and having a predetermined coil-like configuration extending in a plane, a plurality of longitudinally spaced-apart electrodes mounted on the distal end portion, comprising the steps of inserting the distal end portion of the flexible elongate member into the lumen so as to cause the distal end portion to become substantially straight, introducing the distal extremity into the chamber of the heart, causing relative longitudinal movement between the flexible elongate tubular member and the distal end portion so as to cause the distal end portion to slide out of the lumen and assume the coil-like configuration, engaging the wall of the heart with the coil-like configuration and mapping the wall of the heart with the plurality of electrodes to locate the origin of an arrhythmia.

16. A method as in claim 15 wherein the inserting step includes restraining the distal end portion in a substantially straightened shape with the flexible elongate tubular member.

17. A method as in claim 15 together with the step of ablating the wall of the heart.

18. A method of mapping a surface of a wall of a left atrium of a heart having a right atrium with a flexible elongate member having proximal and distal extremities, a handle secured to the proximal extremity, the distal extremity carrying a plurality of longitudinally spaced-apart electrodes and having a free end, comprising utilizing the handle to introduce the distal extremity with the free end into the right atrium, extending the distal extremity through the septum into the left atrium of the heart, causing the distal extremity with the free end to assume a coil-like configuration, engaging the wall of the left atrium with the coil-like configuration and mapping the wall of the atrium with the electrodes carried on the distal extremity with the free end.

19. A mapping and/or ablation catheter for introduction into a chamber formed by a wall of a heart of a human body and accessible by a passage leading to the chamber comprising a flexible elongate tubular member having proximal and distal extremities and extending along a longitudinal axis, the flexible elongate tubular member provided with a lumen extending between the proximal and distal extremities and having a length so that when the distal extremity is in the heart the proximal extremity is outside of the body, a flexible elongate member slidably carried within the lumen and having a distal end portion with a free end, means carried by the proximal extremity of the flexible elongate tubular member for moving the distal end portion between a first position disposed in the lumen in the flexible elongate tubular member and a second position outside of the flexible elongate tubular member, the distal end portion including an element of a shape memory alloy having a predetermined spiral configuration substantially centered on the longitudinal axis when in the second position, the distal extremity of the flexible elongate tubular member serving as means for moving the distal end portion to a substantially straightened configuration when the distal end portion is disposed in the lumen and a plurality of longitudinally spaced-apart electrodes carried by the distal end portion for mapping and/or ablating the wall inside the chamber of the heart.

20. A catheter as in claim 19 wherein the spiral configuration tapers as it extends distally from the flexible elongate tubular member.

21. An endocardial mapping device for introduction into a chamber formed by a wall of a heart of a human body and accessible by a passage leading to the chamber comprising a flexible elongate tubular member extending along a longitudinal axis and having proximal and distal extremities and a lumen extending between the proximal and distal extremities, the flexible elongate tubular member having a length so that when the distal extremity is in the chamber the proximal extremity is outside of the body, a plurality of electrodes, means carried by the distal extremity for supporting the plurality of electrodes in spaced-apart positions lying substantially in a plane, said means including at least one flexible elongate member having a free end and having at least certain of said electrodes mounted thereon in longitudinally spaced-apart positions, the free end of said flexible elongate member including an element of a shape memory alloy having a predetermined conformation so that the electrodes mounted thereon lie in a predetermined pattern, the distal extremity of the flexible elongate tubular member serving as means for moving said flexible elongate member to a substantially straightened conformation when said flexible elongate member is disposed in the lumen said flexible elongate member being slidably movable in the lumen between a first position and a second position so that in the first position the free end of said flexible elongate member is disposed within the lumen and in the second position the free end is disposed distal of the distal extremity of the flexible elongate tubular member whereby the plurality of electrodes engage a portion of the wall when said flexible elongate member is in the second position for permitting high density mapping of the portion of the wall.

22. A device as in claim 21 wherein the element is formed from a superelastic shape memory alloy.

23. A device as in claim 21 wherein said flexible elongate member has a plurality of loops when in the predetermined conformation.

24. A catheter for introduction into a chamber formed by a wall of a heart of a human body in which aberrant electrical signals are traveling in the wall of the heart comprising a flexible elongate member having proximal and distal extremities and extending along a longitudinal axis, the flexible elongate member having a length so that when the distal extremity is disposed in the chamber the proximal extremity is outside of the body, the distal extremity having a coil-like configuration formed from a plurality of turns, a plurality of at least three longitudinally spaced-apart electrodes mounted on separate turns in substantial linear alignment across the coil-like configuration, of the distal extremity lead means connected to the plurality of electrodes and extending to the proximal extremity of the flexible elongate member, means for supplying electrical energy to the plurality of electrodes, the plurality of electrodes being spaced apart so that when electrical energy is supplied to the electrodes a substantially linear lesion is formed in the wall of the heart to interrupt the path of aberrant electrical signals.

25. A device as in claim 21 wherein the plane is disposed at a substantially right angle to the longitudinal axis.

26. A catheter as in claim 24 wherein the distal extremity of the flexible elongate member includes an element of a superelastic shape memory alloy.

27. A catheter as in claim 24 wherein each of the plurality of electrodes is a ring electrode.

* * * * *